(12) United States Patent
Madabhushi et al.

(10) Patent No.: US 10,776,607 B2
(45) Date of Patent: Sep. 15, 2020

(54) PREDICTING PROSTATE CANCER BIOCHEMICAL RECURRENCE AND METASTASIS WITH COMPUTER EXTRACTED FEATURES FROM TUMOR NUCLEI AND BENIGN REGIONS

(71) Applicant: Case Western Reserve University, Cleveland, OH (US)

(72) Inventors: Anant Madabhushi, Shaker Heights, OH (US); Anna Gawlik, St. Charles, IL (US); George Lee, Parlin, NJ (US)

(73) Assignee: Case Western Reserve University, Cleveland, OH (US)

( * ) Notice: Subject to any disclaimer, the term of this patent is extended or adjusted under 35 U.S.C. 154(b) by 190 days.

(21) Appl. No.: 15/983,397

(22) Filed: May 18, 2018

(65) Prior Publication Data

US 2018/0336395 A1 Nov. 22, 2018

Related U.S. Application Data

(60) Provisional application No. 62/508,593, filed on May 19, 2017.

(51) Int. Cl.
*G06K 9/00* (2006.01)
*G06T 7/00* (2017.01)
(Continued)

(52) U.S. Cl.
CPC ..... *G06K 9/00147* (2013.01); *G06K 9/00134* (2013.01); *G06K 9/627* (2013.01);
(Continued)

(58) Field of Classification Search
CPC ............... G06K 9/00147; G06K 9/627; G06K 9/00134; G16H 50/50; G16H 50/30;
(Continued)

(56) References Cited

U.S. PATENT DOCUMENTS 6,025,128 A * 2/2000 Veltri ................. C12Q 1/68
435/6.14
2002/0164063 A1* 11/2002 Heckman ........... G01N 15/1475
382/133

(Continued)

OTHER PUBLICATIONS

Veta et al. "Automatic Nuclei Segmentation in H&E Stained Breast Cancer Histopathology Images" PLoS ONE 8(7):e70221, published on Jul. 29, 2013.

*Primary Examiner* — Ayodeji O Ayotunde
(74) *Attorney, Agent, or Firm* — Eschweiler & Potashnik, LLC

(57) ABSTRACT

Embodiments predict biochemical recurrence (BCR) or metastasis by accessing a set of images of a region of tissue demonstrating cancerous pathology, including a tumor region and a tumor adjacent benign (TAB) region, the set of images including a first stain type image, and a second stain type image; segmenting cellular nuclei represented in the first and second image; generating a combined feature set by extracting at least one feature from each of a tumor region and TAB region represented in the first image, and a tumor region and TAB region represented in the second image, providing the combined feature set to a machine learning classifier; receiving, from the classifier, a probability that the region of tissue will experience BCR or metastasis; and generating a classification of the region of tissue as likely to experience BCR or metastasis, or unlikely to experience BCR or metastasis.

16 Claims, 9 Drawing Sheets

(51) Int. Cl.
| | |
|---|---|
| *G06T 7/60* | (2017.01) |
| *G06T 7/11* | (2017.01) |
| *G16H 30/40* | (2018.01) |
| *G06K 9/62* | (2006.01) |
| *G16H 50/30* | (2018.01) |
| *G16H 50/50* | (2018.01) |
| *G01N 15/14* | (2006.01) |
| *G01N 33/574* | (2006.01) |

(52) U.S. Cl.
CPC .............. *G06T 7/0014* (2013.01); *G06T 7/11* (2017.01); *G06T 7/60* (2013.01); *G16H 30/40* (2018.01); *G16H 50/30* (2018.01); *G16H 50/50* (2018.01); *G01N 15/1475* (2013.01); *G01N 33/57434* (2013.01); *G06T 2207/10024* (2013.01); *G06T 2207/20076* (2013.01); *G06T 2207/20081* (2013.01); *G06T 2207/20084* (2013.01); *G06T 2207/30081* (2013.01); *G06T 2207/30096* (2013.01)

(58) Field of Classification Search
CPC .. G16H 30/40; G06T 7/11; G06T 7/60; G06T 7/0014
USPC ......................................................... 382/133
See application file for complete search history.

(56) References Cited

U.S. PATENT DOCUMENTS

| | | | |
|---|---|---|---|
| 2010/0111396 A1* | 5/2010 | Boucheron | G06K 9/6231 382/133 |
| 2014/0153811 A1* | 6/2014 | Seppo | G06T 7/0012 382/133 |
| 2016/0335478 A1* | 11/2016 | Bredno | A61B 17/3423 |

* cited by examiner

US 10,776,607 B2

PREDICTING PROSTATE CANCER BIOCHEMICAL RECURRENCE AND METASTASIS WITH COMPUTER EXTRACTED FEATURES FROM TUMOR NUCLEI AND BENIGN REGIONS

CROSS REFERENCE TO RELATED APPLICATIONS

This application claims the benefit of U.S. Provisional Application 62/508,593, filed May 19, 2017.

FEDERAL FUNDING NOTICE

This invention was made with government support under grants DK098503, CA179327, CA195152, CA199374, CA202752, RR012463 and CA208236 awarded by the National Institutes of Health. Also, grants W81XWH-13-1-0418, W81XWH-14-1-0323, and W81XWH-16-1-0329 awarded by the Department of Defense. The government has certain rights in the invention.

BACKGROUND

Every year, there are approximately 160,000 new cases of and 26,000 deaths from prostate cancer (PCa) in the United States. The majority of patients diagnosed with PCa in the United States currently opt for a radical prostatectomy procedure which involves surgical excision of the prostate gland. After a radical prostatectomy, a patient's prostate specific antigen (PSA) levels are monitored. If the PSA levels rise above a threshold of 0.2 ng/mL, the patient is determined to have biochemical recurrence (BCR). In some of these patients, the cancer metastasizes, spreading beyond the prostate. BCR occurs in approximately 20-30% of patients within five years of a radical prostatectomy, and metastasis develops in approximately 20% of patients within fifteen years of a radical prostatectomy. Of patients who experience BCR post-surgery, approximately 34% develop metastasis and approximately 70% suffer PCa specific mortality.

Computerized histomorphometric analysis of PCa hematoxylin and eosin (H&E) stained tissue images may be used to predict cancer grade, aggressiveness and risk of biochemical recurrence. Gland angularity may be strongly predictive of BCR in H&E prostate tissue images. Quantitative histomorphometry features of nuclear texture, architecture, and shape extracted from surgically resected H&E tissue images may be predictive of Gleason grade and risk of disease recurrence. For instance, nuclear roundness, alterations in nuclear structure, and morphometry acquired from H&E stained images may be useful in predicting cancer progression, outcome, and BCR. Nuclear shape and arrangement as characterized by Voronoi and Delaunay Triangulation graphs may also be predictive of BCR.

Other existing approaches to predicting BCR use QH features calculated from Feulgen stained images. The Feulgen stain binds with DNA within the nucleus of the cell and thus provides functional characterization of the cancer. The level of dye that each cell uptakes in the Feulgen stain is correlated to the amount of DNA it contains. The extent of Feulgen staining may be linked with cancer presence and aggressiveness. Some approaches use nuclear architecture and texture to characterize Feulgen stained images to predict patient outcome. Combining measurements relating to nuclear size, shape, and texture from Feulgen stained images may facilitate prediction of progression of prostate cancer. Nuclear size and shape, DNA content, and texture features relating to chromatin organization may be predictive of BCR, metastasis, and PCa specific death.

The aforementioned existing approaches focus on histomorphometric features extracted from within the tumor region to predict BCR and metastasis. However, tumor adjoining benign appearing regions may be relevant to predicting disease outcome. Nuclear morphometric features from within tumor adjacent benign (TAB) regions on surgically resected prostate specimens may be more predictive of BCR than corresponding features from within the tumor. One existing approach employs simple features related to nuclear shape to predict metastasis in PCa.

While a number of molecular assays for predicting PCa risk, BCR, progression, and metastasis have been proposed, all of these tests have tended to be tissue destructive. Additionally, these existing tests involve molecular measurements being assessed from the tumor region alone and hence may not capture a comprehensive portrait of intratumoral heterogeneity, and are thus sub-optimal in their predictive ability for predicting disease aggressiveness and outcome. Furthermore, apart from the deleterious side-effects of chemotherapy to the patient, in this era of spiraling healthcare costs, it must also be noted that these treatments are remarkably expensive. Consequently, there is a clinical unmet need for identifying PCa patients at elevated risk for BCR and metastasis who will receive added benefit from chemotherapy post-surgery.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that, in some examples, one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
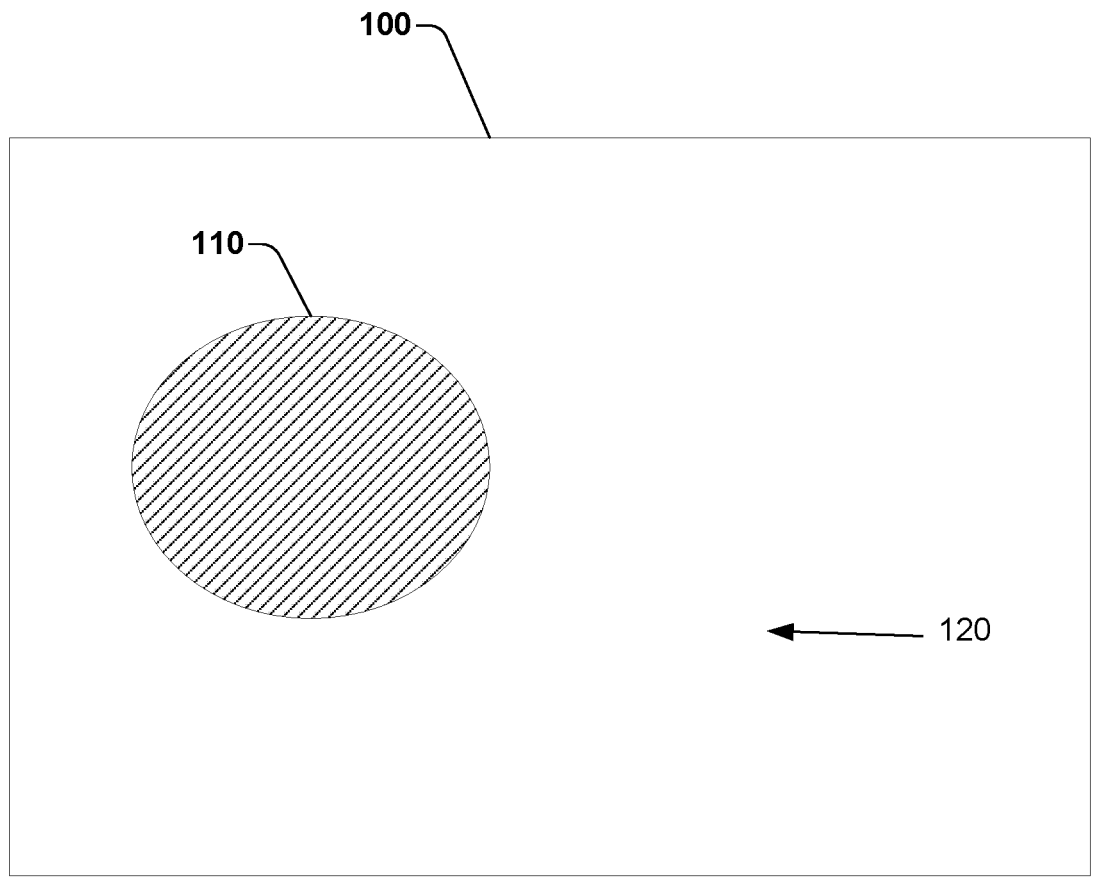
FIG. 1 illustrates a region of tissue including a tumor region and a tumor adjacent benign region.

Embodiments described herein predict risk of BCR or metastasis following radical prostatectomy using a combination of computer extracted features of nuclear morphology and architectural arrangement from within tumor and tumor adjacent-benign (TAB) regions of Feulgen stained images and H&E stained images. Embodiments provide a combination of features extracted from tumor and TAB regions of Feulgen and H&E stained images to a machine learning classifier which computes a probability that the region of tissue from which the features were extracted will experience BCR or metastasis based, at least in part, on the combination of extracted features. Embodiments are more predictive of outcome (e.g., BCR or metastasis) compared to existing approaches that employ features extracted from within the tumor alone, that employ only a single category of features, or that that extract features from a single stain type only.

In one embodiment, digitized images of surgical tissue specimens in the form of tissue microarrays (TMAs) for 260 prostate cancer patients are accessed. The excised prostates are sectioned, stained with H&E and Feulgen, and digitized at a resolution of 0.5 micron per pixel. In each TMA, tumor, TAB, and control regions are included as 0.6 mm images. A representative image is chosen from each TMA and reviewed by an expert human pathologist.

Seven TMAs are employed in this embodiment. The patients from five of the TMAs were selected to create a cohort with split metastasis outcomes. The patients from two of the TMAs were selected to have a grade-stratified group based on Gleason grade. The patients were not selected specifically for this embodiment. Each TMA included 40 patients other than one TMA, which contained 35 patients. Because of a lack of follow-up data, fifteen patients were not considered. This left a total of usable cases from 260 patients. This cohort of 260 patients in turn comprised 210 patients who experienced BCR within 10 years, while 50 patients did not experience BCR. Additionally the cohort also comprised 132 PCa patients who went on to have metastasis following surgery, and another 128 patients who did not experience metastasis within 10 years.

In this embodiment, a watershed-based segmentation approach is used for nuclei segmentation. Nuclei segmentation is performed though the following steps. First, an intensity gradient is applied at each pixel in an image to define gradient thresholds at multiple scales. Second, multiple markers including morphological operations, fast radial symmetry transform, regional minima extraction, and marker-controlled watershed are applied at multiple scales to perform a watershed segmentation. Third, post-processing of the image is used to remove irrelevant structures and false positive regions that do not contain nuclei using size thresholding. The regions that remain are parameterized as ellipses. Fourth, results from all scales are merged by resolving concurrent regions to yield one final segmentation. Segmentation in this embodiment is done on the entire set of H&E and Feulgen stained images. In other embodiments, other segmentation techniques may be employed.

In this embodiment, the segmented nuclei are used to calculate 242 features for each stain type and from both within the tumor and TAB region for each patient. The extracted features may be grouped into five categories: Global Cell-Graph, Local Cell-Graph, Shape, Cell Orientation Entropy (COrE), and Texture Features. To calculate the Graph features, nuclear centroids are used to create a Voronoi diagram, Delaunay Triangulation plot, and Minimum Spanning Tree for each TMA core image. To create a Voronoi diagram, regions are created around the designated points of the segmented nuclei. These regions contain the areas in the stained image that are closest to that particular nucleus. These regions are used to calculate features based on area, perimeter, and line segments. To create a Delaunay Triangulation plot, the centroids of the segmented nuclei are used to create triangles that maximize the minimum angle from all of the angles in all of the triangles in the plot. These triangles are used to calculate features based on side length and triangle area. A Minimum Spanning Tree (MST) connects all of the nuclei with the shortest paths between them and is used to calculate features involving edge length of the MST.

In this embodiment, from the different nuclear graph plots, a plurality of nuclear features is extracted, including the number of and distance to neighboring nuclei. COrE features are calculated by using dominant orientations of the individual cells to measure contrast and intensity energy, inverse moment, entropy, average, and variance. To create cluster graphs for extracting the COrE features, the nuclei are grouped into clusters defined by a distance threshold between nuclei. The distance may be user-selectable. The features calculated from these clusters include statistics pertaining to the isolated, end, and central nodes, edge and path amounts and length, connected components, clustering coefficients, and degrees. Haralick features for characterizing nuclear texture are found with a gray-level co-occurrence matrix, the size of the co-occurrence matrix corresponding to the number of unique gray levels in the image. Within the matrix, the elements represent the probability that a pixel of a certain value will be adjacent to a pixel of a different value, a measure of the distribution of intensities. This matrix is used to extract contrast, intensity, probability, correlation, and information features in order to describe the internal heterogeneity within the nucleus.

In this embodiment, a machine learning classifier is trained and tested using a training set of images and a testing set of images. To create training and testing sets, the TMAs are randomized. For the biochemical recurrence outcome predictions, 30 BCR and 24 NR patients are selected for the training set. The remaining 180 BCR and 26 NR patients are used for the testing set. This creates a smaller and balanced training set of 54 patients and testing set of 206 patients. For the metastasis predictions, the entire patient set is split in half and 66 metastasis and 64 non-metastasis patients are designated for the training and testing sets, creating equal sets of 130 patients. A second metastasis prediction testing set is made with 206 patients: 102 metastasis and 104 non-metastasis.

In this embodiment, a minimum redundancy maximum relevance (MRMR) feature selection scheme is applied to the features of the H&E and Feulgen images included in the BCR and Mets training sets. This feature selection scheme is applied to the training set of features extracted from: the H&E stained tumor region, the H&E TAB region, the Feulgen tumor region, the Feulgen TAB region, the combination of H&E and Feulgen stained tumor images, and the combination of H&E and Feulgen TAB regions. The MRMR scheme used in this embodiment employs three-fold cross-validation with 100 iterations to rank the most significant features for each combination of input features. This process is done with the BCR training set of 54 patients and determines features significant in predicting BCR. In another embodiment, the MRMR feature selection process is further applied to the metastasis training set, and determines features significant in predicting metastasis. In another embodiment, other feature selection approaches may be employed.

In this embodiment, the machine learning classifier is trained from the ranked features. From the ranked features determined by MRMR, the 10 most significant features are used to train, in this embodiment, a Random Forest classifier to predict biochemical recurrence. In another embodiment, the machine learning classifier, or a second, different machine learning classifier, is further trained to predict metastasis. The following classifiers were built using feature sets: H&E features from tumor regions ($C_{H\_T}$), H&E features from tumor and benign regions (TB) ($C_{H\_TB}$), Feulgen features from tumor regions ($C_{F\_T}$), Feulgen features from TB ($C_{F\_TB}$), the combination of H&E and Feulgen QH features from tumor regions ($C_{HF\_T}$), and the combination of H&E and Feulgen features from TB ($C_{HF\_TB}$). The classifiers made with the features of the training set of BCR patients were applied to the testing set of 206 BCR patients to predict BCR and to the testing set of 206 metastasis patients to predict metastasis. In another embodiment, the classifiers made with the features of the training set of metastasis patients were applied to the testing set of 130 patients to predict metastasis. In another embodiment, other types of machine learning classifiers, including support vector machine (SVM) classifiers or convolutional neural networks (CNN) may be trained and employed.

In this embodiment, when MRMR selection was applied to the H&E TB features, five out of the top ten features were calculated on nuclei in a benign region and the other five features were from the tumor region, indicating that for the H&E stain, both image regions (i.e., tumor and TAB) had features predictive of BCR. Shape and texture (Haralick) features made up the majority of significant features. Four shape, four Haralick, one Cell-graph, and one COrE feature made up the top ten. The H&E stains the morphological pattern within the tissue and facilitates identifying multiple cellular structures, supporting the multiple feature types that were identified as discriminable, and several shape features were significant. For features that were found to be significant from the entire Feulgen set, six of the top 10 were from the benign region, suggesting that the benign region of Feulgen stained images offers greater predictive potential than the tumor region. The significant features were split with six shape and four Haralick features in the top ten.

In this embodiment, when H&E and Feulgen TB features were used in combination with each other to predict BCR, seven of the top ten features were from the H&E stain. Although the H&E stain may have the majority of significant features, the functional information derived from the Feulgen stain adds to the morphological information from the H&E stain. Six of the features were from the tumor region. Of the top features, six were Haralick features, three were shape features, and one was a cell-graph feature. Of the three significant Feulgen features, two were Haralick. Although a majority of significant features in the Feulgen-only feature set were shape features, once the H&E and Feulgen features were combined, the texture features proved to be more significant than shape features. The variety of significant H&E features in the combination reflected the variety of feature types in the H&E-only feature set.

Embodiments described herein demonstrably improve on existing approaches to predicting BCR or metastasis by providing improved accuracy. The predictions of BCR machine learning classifiers built using features from the tumor regions of images ($C_{H\_T}$, $C_{F\_T}$, $C_{HF\_T}$) and those built with using tumor and benign regions of images ($C_{H\_TB}$, $C_{F\_TB}$, $C_{HF\_TB}$) were compared with each other, and with existing approaches. Using the Gleason score ($C_G$), the Area Under Curve (AUC) and accuracy of BCR predictions was 0.486 and 49.9%. Kattan ($C_K$) and Stephenson ($C_S$) nomograms had AUC and accuracy values of 0.702 and 66.5% and 0.761 and 70.4%, respectively. With a p-value of 0.401, $C_G$ was found to not be a statistically significant predictor while $C_K$ and $C_S$ were statistically significant with values of 0.00467 and 0.000307. Of predictors made with features from the H&E stain, when only using features from the tumor region ($C_{H\_T}$), the classifier resulted in an AUC of 0.95, an accuracy of 95.6% and a p-value of $1.45^{-5}$. Embodiments described herein, using features from both regions ($C_{H\_TB}$), resulted in an AUC of 0.941, accuracy of 92.7%, and p-value of $9.11^{-7}$. The predictions made with $C_{H\_TB}$ had a higher hazard ratio and concordance index than $C_{H\_T}$. Using the tumor features ($C_{F\_T}$) and TB features ($C_{F\_TB}$) of the Feulgen stain, the embodiments described herein achieved an AUC, accuracy, and p-value of 0.836, 83%, and 0.0093 and 0.969, 93.7%, and 0.0032, respectively. For embodiments described herein that use the different stain types together in a combination H&E and Feulgen classifier, the AUC, accuracy, and p-value of $C_{HF\_T}$ were 0.967, 95.6%, and $4.05^{-6}$ and the values of $C_{HF\_TB}$ were 0.973, 94.2%, and $4.24^{-11}$. The top-ranked features of stains in combination with each other for both types of regions resulted in better BCR predictions compared to existing clinical methods.

In one embodiment, the features found to be predictive of BCR were applied to a metastasis training set of 206 patients. With this metastasis testing set, the statistics of the conventional clinical predictors were an AUC and accuracy of 0.516 and 51.9% for $C_G$, 0.575 and 56.3% for $C_K$ and 0.569 and 52.9% for $C_S$. Of existing approaches, only the prediction made with the Stephenson nomogram was statistically significant with a p-value of 0.00056. When the BCR features were applied to the metastasis training set of H&E images, $C_{H\_T}$ had an AUC value of 0.677 and a prediction accuracy of 68.5% while $C_{H\_TB}$ had an AUC and accuracy of 0.692 and 67.5%. The significant features applied to the Feulgen stained images resulted in an AUC and accuracy value of 0.674 and 67.5% for $C_{F\_T}$ and 0.706 and 69.9% for $C_{F\_TB}$. The predictions made with TB had a higher accuracy and AUC. For the combination of stains, the AUC and accuracy of $C_{HF\_T}$ and $C_{HF\_TB}$ were 0.717 and 68% and 0.731 and 68.9%, respectively. All p-values of classifiers made with QH features from the H&E and Feulgen stained images indicate statistically significant predictions. $C_{HF\_TB}$ had the highest AUC of all metastasis predictions made with BCR features.

Embodiments described herein predict BCR or metastasis with greater accuracy than existing approaches that may only use very simple features relating to nuclear shape. Embodiments use a canon of more advanced features relating to texture and architectural arrangement, providing greater discrimination between classes. By increasing the accuracy with which a patient's likelihood of experiencing BCR or metastasis is predicted, example methods and apparatus produce the concrete, real-world technical effect of increasing the probability that at-risk patients receive timely treatment tailored to the particular pathology they exhibit. The additional technical effect of reducing the expenditure of resources and time on patients who have a less aggressive pathology is also achieved. Example embodiments further improve on existing approaches by providing a more accurate second reader to facilitate the reduction of inter-reader and intra-reader variability among human radiologists, pathologists, or oncologists. Example methods and apparatus thus improve on existing methods in a measurable, clinically significant way. When implemented as part of a personalized medicine system, a computer assisted diagnostic (CADx) system, or a BCR or metastasis prediction system which may include a computer or a processor configured to predict BCR or metastasis, example embodiments improve the performance of a machine, computer, or computer-related technology by providing a more accurate and more reliable prediction of disease recurrence or metastasis compared to existing approaches to controlling a machine to predict disease recurrence or metastasis.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 2:
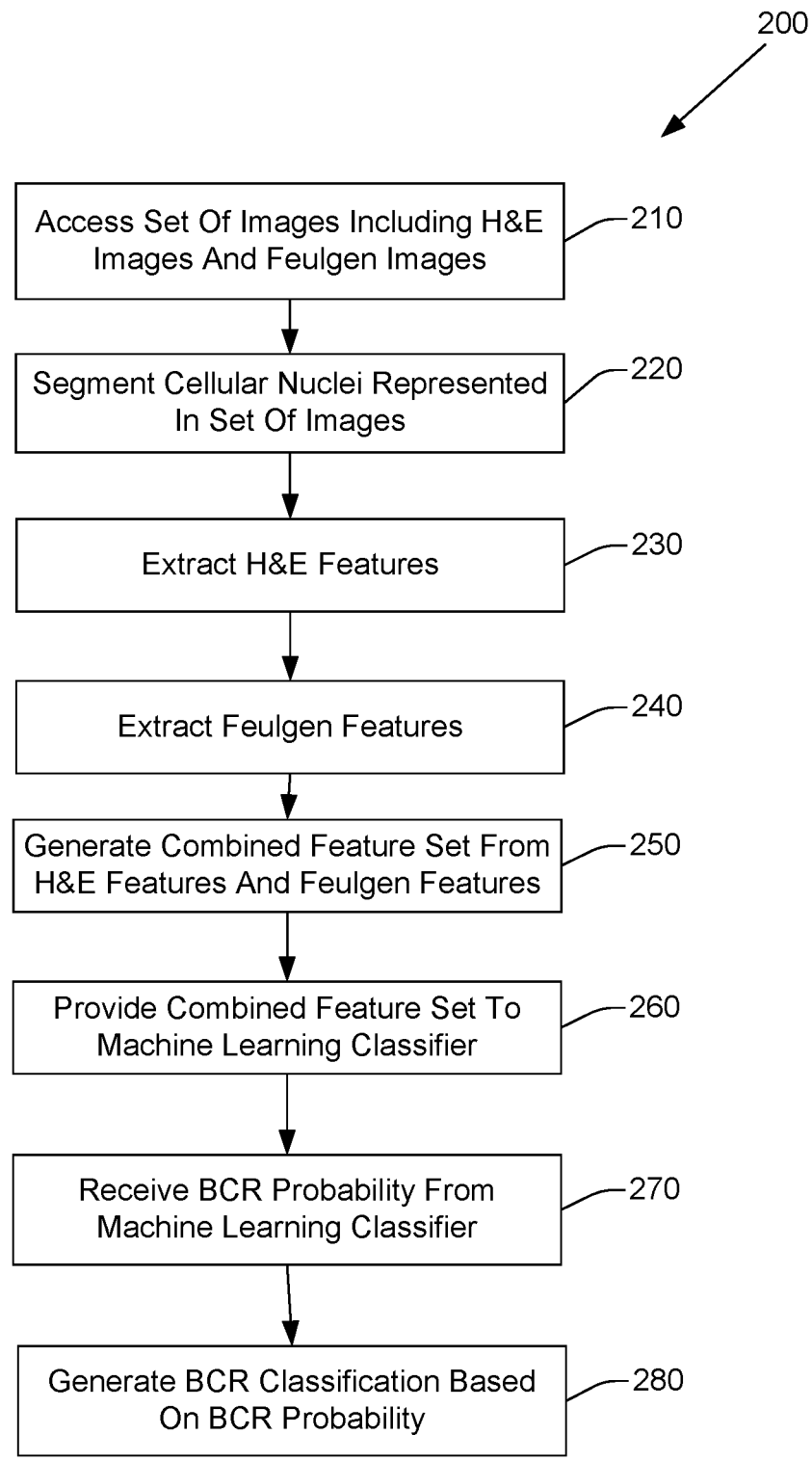
FIG. 2 is a schematic overview of an exemplary workflow for biochemical recurrence (BCR) prediction.

FIG. 2 is a flow diagram of an example set of operations 200 that may be performed by a processor for predicting BCR or metastasis. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations. The memory or storage devices may include main memory, disk storage, or any suitable combination thereof. The memory or storage devices may include, but are not limited to volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage. The memory or storage devices may be configured to store a set of images of a region of tissue demonstrating PCa.

The set of operations 200 includes, at 210, accessing a set of images of a region of tissue demonstrating PCa. Accessing the set of images includes acquiring electronic data, reading from a computer file, receiving a computer file, reading from a computer memory, or other computerized activity. A member of the set of images has a plurality of pixels, a pixel having an intensity. The region of tissue includes a tumor region and a TAB region. The set of images includes a digitized H&E stained image, and a digitized Feulgen stained image. In one embodiment, the H&E stained image is a digitized image of an H&E slide of the region of tissue scanned at a resolution of 0.5 microns per pixel. In this embodiment, the Feulgen stained image is a digitized image of a Feulgen stained slide of the region of tissue scanned at a resolution of 0.5 microns per pixel. In other embodiments, the set of images may be of other, different types of tissue demonstrating other, different pathologies, or may be acquired using different imaging techniques, staining techniques, or parameters. FIG. 1 is a simplified representation of an example member of the set of images that includes a region of tissue 100. The region of tissue 100 includes a tumor region 110, and a TAB region 120.

The operations 200 also includes, at 220, segmenting cellular nuclei represented in the H&E stained image, and segmenting cellular nuclei represented in the Feulgen stained image. In one embodiment, segmenting cellular nuclei includes controlling the processor to perform operations including segmenting cellular nuclei using a watershed approach. In another embodiment, other segmentation techniques may be employed, including deep learning based, deformable approaches such as active contours, level sets, or thresholding based techniques.

Figure 5:
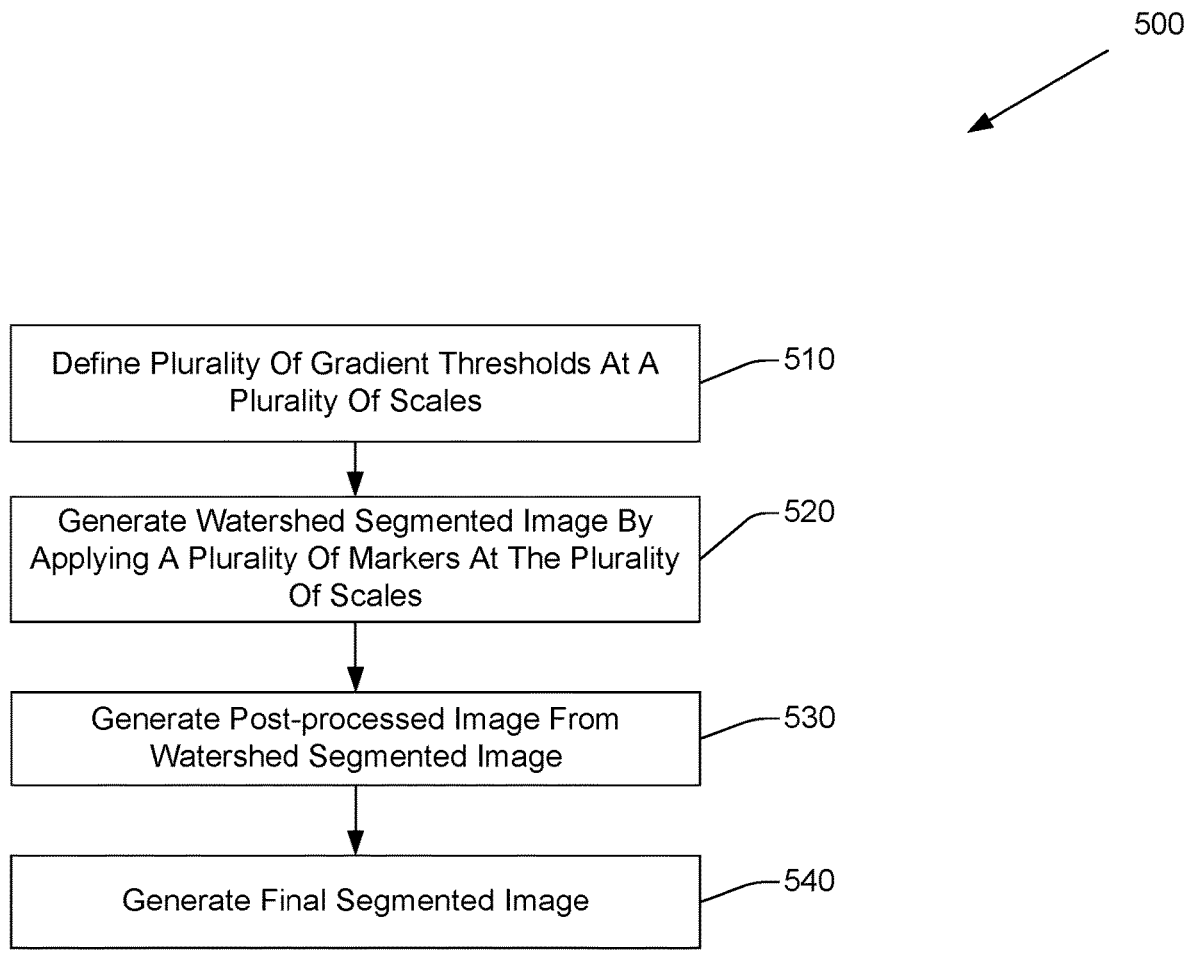
FIG. 5 illustrates an example method for segmenting nuclei represented in an image of a region of tissue demonstrating PCa.

FIG. 5 is a flow diagram of an example method 500 for segmenting cellular nuclei using a watershed approach suitable for use by embodiments described herein. Method 500 may, in one embodiment, be implemented as a set of operations that when executed control a processor to perform operations that correspond to method 500. Method 500 includes, at 510 defining a plurality of gradient thresholds at a plurality of scales respectively by applying an intensity gradient to a threshold number of pixels in the image. The threshold number of pixels may include all the pixels in the image, or some portion of the all the pixels in the image (e.g., 90%, 75%). Method 500 also includes, at 520, generating a watershed segmented image by performing a watershed segmentation by applying a plurality of markers at the plurality of scales. In one embodiment, the plurality of markers includes a morphological operation, a fast radial symmetry transform, and a regional minima extraction. Method 500 also includes, at 530, generating a post-processed image by removing false positive regions from the watershed segmented image using size thresholding, and parameterizing the regions remaining in the post-processed image as ellipses. Method 500 further includes, at 540, generating a final segmented image by merging results from the plurality of scales by resolving concurrent regions.

Returning to FIG. 2, the operations 200 also include, at 230, extracting a first set of radiomic features from the H&E stained image. The first set of radiomic features is extracted based, at least in part, on the segmented nuclei. In one embodiment, the first set of radiomic features include a global cell graph feature, a local cell graph feature, a shape feature, a cell orientation entropy (COrE) feature, and a texture feature. In one embodiment, a global cell graph feature or a local cell graph feature may be a Voronoi diagram, a Delaunay triangulation plot, or a minimum spanning tree. In another embodiment, a global cell graph feature or a local cell graph feature may be another, different type of global cell graph feature or local cell graph feature.

The operations 200 also include, at 240, extracting a second set of radiomic features from the Feulgen stained image. The second set of radiomic features is extracted based, at least in part, on the segmented nuclei. In one embodiment, the second set of radiomic features includes a global cell graph feature, a local cell graph feature, a shape feature, a COrE feature, and a texture feature. In one embodiment, a global cell graph feature or a local cell graph feature may be a Voronoi diagram, a Delaunay triangulation plot, or a minimum spanning tree. In another embodiment, a global cell graph feature or a local cell graph feature may be another, different type of global cell graph feature or local cell graph feature. The first set of radiomic features and the second set of radiomic features are sub-visual features that cannot be perceived by the human eye or extracted by pencil and paper.

The operations 200 also include, at 250, generating a combined feature set from the first set of radiomic features and the second set of radiomic features. The combined feature set includes at least one feature extracted from the tumor region represented in the H&E stained image and at least one feature extracted from the TAB region represented in the H&E stained image. The combined feature set further includes at least one feature extracted from the tumor region represented in the Feulgen stained image and at least one feature extracted from the TAB region represented in the Feulgen stained image. In one embodiment, the combined feature set includes at least ten features. In another embodiment, the combined feature set may include other different numbers of features. The features included in the combined feature set may be based on an MRMR feature selection approach, in which the top most significant features (e.g., 10 most significant features) are selected and included in the combined feature set.

The operations 200 also include, at 260, providing the combined feature set to a machine learning classifier. Providing the combined feature set to the machine learning classifier includes acquiring electronic data, reading from a computer file, receiving a computer file, reading from a computer memory, or other computerized activity. In one embodiment, the machine learning classifier is a random forest classifier. In another embodiment, the machine learning classifier may be a linear discriminant analysis (LDA) classifier, a support vector machine (SVM) classifier, a convolutional neural network (CNN) classifier, or other type of machine or deep learning classifier.

The operations 200 also include, at 270, receiving, from the machine learning classifier, a probability that the region of tissue will experience biochemical recurrence (BCR). The machine learning classifier computes the probability based, at least in part, on the combined feature set. Receiving the combined feature set from the machine learning classifier includes acquiring electronic data, reading from a computer file, receiving a computer file, reading from a computer memory, or other computerized activity.

The operations 200 further include, at 280, generating a classification of the region of tissue as likely to experience BCR or unlikely to experience BCR. The classification is based, at least in part, on the probability. For example, in one embodiment, the region of tissue may be classified as likely to experience BCR if the machine learning classifier provides a probability greater than 0.5, while the region of tissue may be classified as unlikely to experience BCR if the probability is less than or equal to 0.5. In another embodiment, the region of tissue may be classified as likely to experience BCR if the probability has another, different value, for example 0.6, 0.75, or 0.9. In one embodiment, the classification may be based on the probability and at least one of the set of images, the first set of radiomic features, the second set of radiomic features, or the combined feature set.

In one embodiment, the operations 200 further include training the machine learning classifier. In this embodiment, the machine learning classifier is trained and tested using a training set of images and a testing set of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed.

Figure 3:
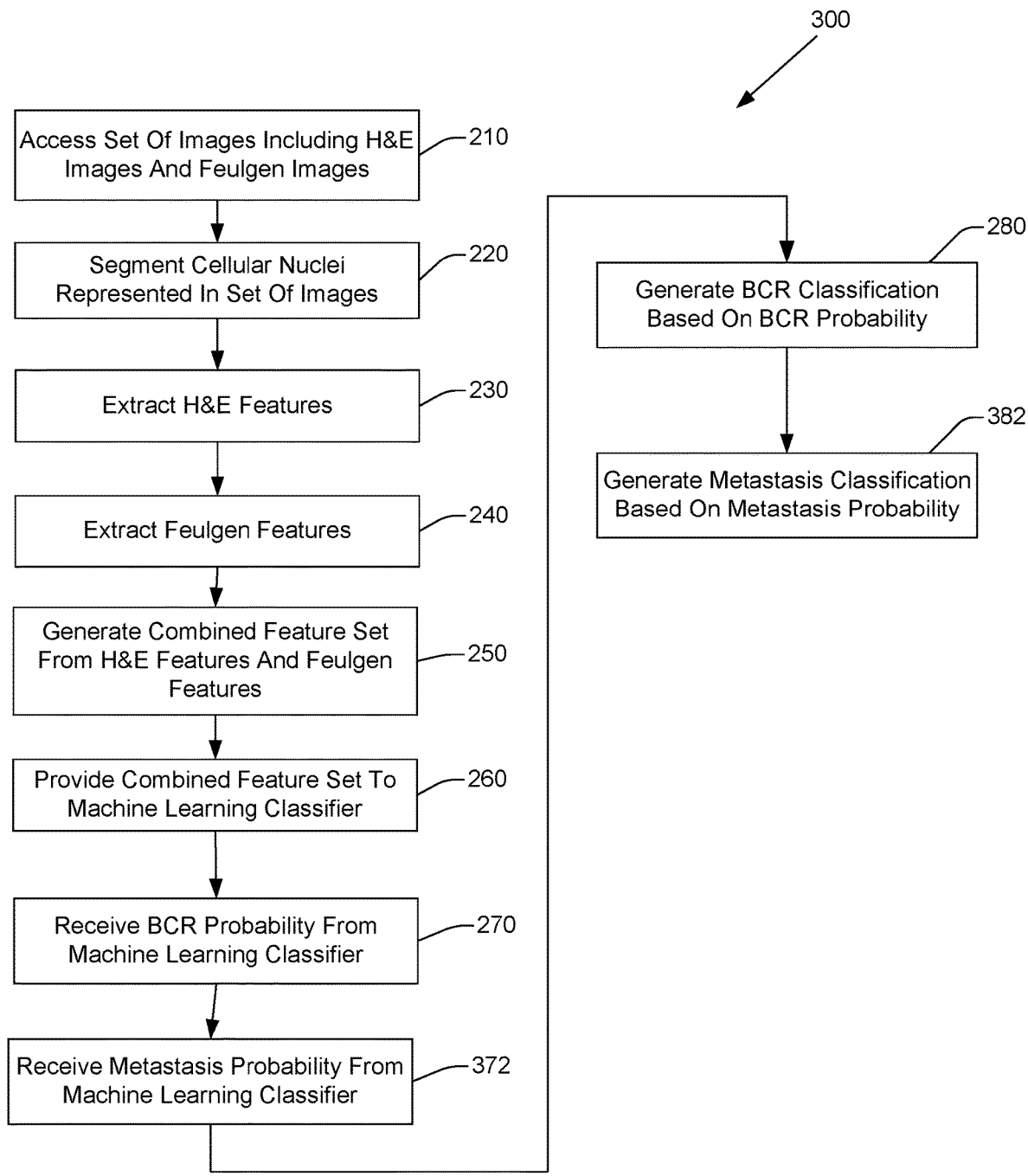
FIG. 3 is a schematic overview of an exemplary workflow for BCR and metastasis prediction.

FIG. 3 is a flow chart of an example set of operations 300 that is similar to the example set of operations 200, but that includes additional operations. The operations 300 further includes, at 372 receiving, from the machine learning classifier, a second probability that the region of tissue will experience metastasis. The machine learning classifier computes the second probability based, at least in part, on the combined feature set.

The operations 300 further include, at 382, generating a second classification of the region of tissue as likely to experience metastasis or unlikely to experience metastasis. The second classification of the region of tissue as likely to experience metastasis or unlikely to experience metastasis is based, at least in part, on the second probability. For example, in one embodiment, the region of tissue may be classified as likely to experience metastasis if the machine learning classifier provides a second probability greater than 0.5. In another embodiment, the region of tissue may be classified as likely to experience metastasis if the second probability has another, different value, for example 0.6, 0.75, or 0.9. In one embodiment, the second classification may be based on the second probability and at least one of the set of images, the first set of radiomic features, the second set of radiomic features, or the combined feature set.

In one embodiment, the combined feature set may be a first combined feature set that includes a median Fourier descriptor 1 shape feature, a standard deviation intensity contrast energy Haralick feature, and a number of central nodes cell graph feature acquired from the tumor region of the H&E stained image. In this embodiment, the combined feature set also includes a mean intensity contrast energy Haralick feature, a median Fourier descriptor 1 shape feature, a standard deviation intensity contrast energy Haralick feature, and a standard deviation intensity contrast average Haralick feature acquired from the TAB region of the H&E stained image. In this embodiment, the combined feature set also includes a mean intensity contrast energy Haralick feature, and a mean Fourier descriptor 7 shape feature acquired from the TAB region of the Feulgen stained image. In this embodiment, the combined feature set further includes a standard deviation intensity average Haralick feature acquired from the tumor region of the Feulgen stained image.

In another embodiment, the combined feature set may be a second combined feature set that includes a median Fourier descriptor 1 shape feature, a min/max invariant moment 3 shape feature, a standard deviation distance to 5 nearest neighbors nuclear architecture feature, and a min/max invariant moment 4 shape feature acquired from the tumor region of the H&E stained image. In this embodiment, the combined feature set also includes a mean Fourier descriptor 9 shape feature, a median Fourier descriptor 1 shape feature, and a standard deviation invariant moment 5 shape feature extracted from the TAB region of the H&E stained image. In this embodiment, the combined feature set also includes a min/max perimeter ratio shape feature, and median Fourier descriptor 1 shape feature extracted from the TAB region of the Feulgen stained image. In this embodiment, the combined feature set further includes a standard deviation invariant moment 1 shape feature extracted from the tumor region of the Feulgen stained image.

In one embodiment, providing the combined feature set to the machine learning classifier includes providing the first combined feature when the machine learning classifier computes the probability that the region of tissue will experience BCR. In another embodiment, the second combined feature set is provided to the machine learning classifier when the machine learning classifier computes the second probability that the region of tissue will experience metastasis. In another embodiment, the first combined feature set is provided to the machine learning classifier when the machine learning classifier computes both the probability that the region of tissue will experience BCR and the second probability that the region of tissue will experience metastasis.

Figure 4:
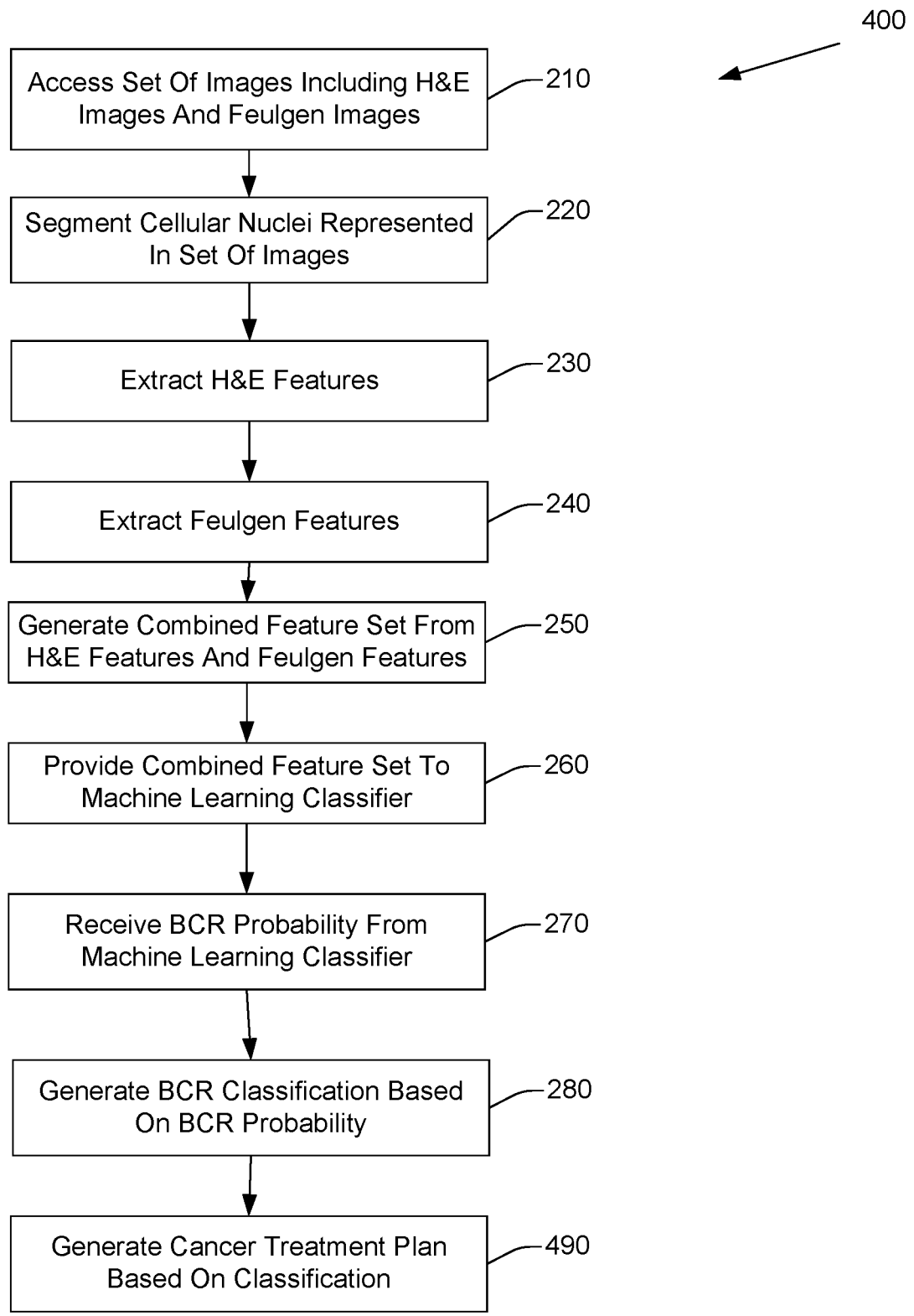
FIG. 4 is a schematic overview of an exemplary workflow for BCR prediction.

FIG. 4 is a flow chart of an example set of operations 400 that is similar to the example set of operations 200 and 300, but that includes additional operations. The operations 400 also include, at 490, generating a PCa treatment plan based, at least in part, on the classification or the second classification. The PCa treatment plan is generated for the patient of which the image was acquired based, at least in part, on the classification or the second classification, and at least one of the probability, the second probability, the combined set of features, or the image. Defining a personalized cancer treatment plan facilitates delivering a particular treatment that will be therapeutically active to the patient, while minimizing negative or adverse effects experienced by the patient. For example, the cancer treatment plan may suggest a surgical treatment, may define an immunotherapy agent dosage or schedule, or a chemotherapy agent dosage or schedule, for a patient identified as likely to experience BCR or metastasis. For a patient classified as unlikely to experience BCR or metastasis, other treatments may be suggested.

FIG. 5 is an illustration of a method 500 for segmenting cellular nuclei suitable for use by embodiments described herein. FIG. 5 illustrates steps for using a watershed segmentation approach. Method 500 includes, at 510, defining a plurality of gradient thresholds at a plurality of scales respectively by applying an intensity gradient to a threshold number of pixels in the image.

Method 500 also includes, at 520, generating a watershed segmented image by performing a watershed segmentation by applying a plurality of markers at the plurality of scales. In one embodiment, the plurality of markers includes a morphological operation, a fast radial symmetry transform, and a regional minima extraction. In another embodiment, other markers may be employed.

Method 500 also includes, at 530, generating a post-processed image by removing false positive regions from the watershed segmented image. False positive regions may be removed using size thresholding. In another embodiment, false positive regions may be removed using other, different techniques. Generating the post-processed image further includes parameterizing the regions remaining in the post-processed image as ellipses.

Method 500 further includes, at 540, generating a final segmented image by merging results from the plurality of scales by resolving concurrent regions. While a watershed segmentation approach is described, other segmentation approaches or techniques may be employed by embodiments described herein. For example, in one embodiment, a deformable contour based approach that employs level sets or active contours, a thresholding based approach, or a deep learning approach may be employed.

Figure 6:
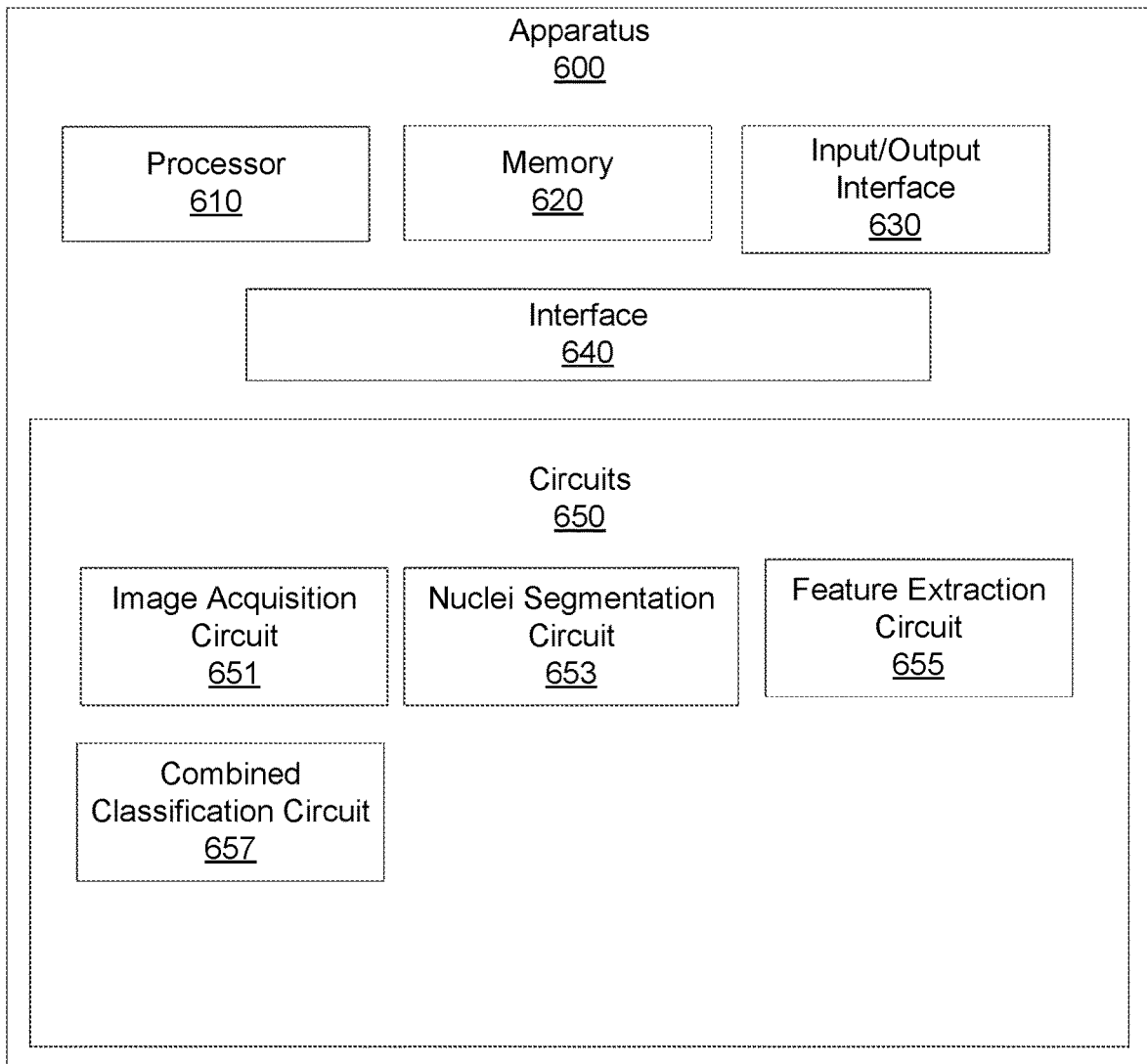
FIG. 6 illustrates an example apparatus for predicting BCR or metastasis.

FIG. 6 illustrates an example apparatus 600 for predicting PCa BCR or metastasis. Apparatus 600 includes a processor 610. Apparatus 600 also includes a memory 620. Processor 610 may, in one embodiment, include circuitry such as, but not limited to, one or more single-core or multi-core processors. Processor 610 may include any combination of general-purpose processors and dedicated processors (e.g., graphics processors, application processors, etc.). The processors may be coupled with or may include memory (e.g. memory 620) or storage and may be configured to execute instructions stored in the memory or storage to enable various apparatus, applications, or operating systems to perform the operations. Memory 620 is configured to store a digitized image of a region of tissue demonstrating cancerous pathology.

In one embodiment, memory 620 is configured to store a set of digitized images of a region of tissue demonstrating PCa. A member of the set of digitized images includes a plurality of pixels, a pixel having an intensity. The region of tissue represented in the image includes a tumor region and a TAB region.

Apparatus 600 also includes an input/output (I/O) interface 630. Apparatus 600 also includes a set of circuits 650. The set of circuits 650 includes an image acquisition circuit 651, a nuclei segmentation circuit 653, a feature extraction circuit 655, and a combined classification circuit 657. Apparatus 600 further includes an interface 640 that connects the processor 610, the memory 620, the I/O interface 630, and the set of circuits 650.

Image acquisition circuit 651 is configured to access the set of digitized images. The set of digitized images includes an H&E stained image of the region of tissue, and a Feulgen stained image of the region of tissue. Accessing the set of digitized images includes acquiring electronic data, reading from a computer file, receiving a computer file, reading from a computer memory (e.g., memory 620), or other computerized activity. In another embodiment, accessing the image may include accessing a network attached storage (NAS), a cloud storage system, or other type of electronic storage system. Accessing the set of digitized images may, in one embodiment, include accessing a NAS device, a cloud storage system, or other type of electronic storage system using input/output interface 630.

Nuclei segmentation circuit 653 is configured to segment cellular nuclei represented in the H&E stained image and the Feulgen stained image. In one embodiment, nuclei segmentation circuit 653 is configured to segment cellular nuclei represented in the H&E stained image and the Feulgen stained image using a watershed approach. In another embodiment, other segmentation approaches or techniques may be employed. In one embodiment, apparatus 600 may be provided with a set of digitized images in which the nuclei have already been segmented.

Feature extraction circuit 655 is configured to extract an H&E set of radiomic features from the tumor region and the TAB region of the H&E stained image. Feature extraction circuit 655 is configured to extract the H&E set of radiomic features from the tumor region and the TAB region of the H&E stained image based, at least in part, on the segmented nuclei.

In one embodiment, the H&E set of radiomic features includes a global cell graph feature, a local cell graph feature, a shape feature, a cell orientation entropy (COrE) feature, and a texture feature. In one embodiment, a global cell graph feature or a local cell graph feature may be a Voronoi diagram, a Delaunay triangulation plot, or a minimum spanning tree. In another embodiment, a global cell graph feature or a local cell graph feature may be another, different type of global cell graph feature or local cell graph feature.

Feature extraction circuit 655 is also configured to extract a Feulgen set of radiomic features from the tumor region and the TAB region of the Feulgen stained image based, at least in part, on the segmented nuclei.

In one embodiment, the Feulgen set of radiomic features includes a global cell graph feature, a local cell graph feature, a shape feature, a cell orientation entropy (COrE) feature, and a texture feature. In one embodiment, a global cell graph feature or a local cell graph feature may be a Voronoi diagram, a Delaunay triangulation plot, or a minimum spanning tree. In another embodiment, a global cell graph feature or a local cell graph feature may be another, different type of global cell graph feature or local cell graph feature. The H&E set of radiomic features and the Feulgen set of radiomic features are sub-visual features that cannot be perceived by the human eye or extracted by pencil and paper.

Feature extraction circuit 655 is also configured to generate a combined feature set from the H&E set and the Feulgen set. The combined feature set includes at least one feature extracted from each of the tumor region and the TAB region of the H&E stained image, and at least one feature extracted from each of the tumor region and the TAB region of the Feulgen stained image.

In one embodiment, the combined feature set includes a global cell graph feature, a local cell graph feature, a shape feature, a COrE feature, and a texture feature. In one embodiment, the combined feature set includes at least ten features. In another embodiment, the combined feature set may include other different numbers of features.

Feature extraction circuit 655 is further configured to provide the combined feature set to combined classification circuit 657. Providing the combined feature set to combined classification circuit 657 may include acquiring electronic data, reading from a computer file, receiving a computer file, reading from a computer memory, or other computerized activity.

Combined classification circuit 657 is configured to receive the combined feature set from feature extraction circuit 655. Receiving the combined feature set from feature extraction circuit 655 may include acquiring electronic data, reading from a computer file, receiving a computer file, reading from a computer memory, or other computerized activity.

Combined classification circuit 657 is also configured to compute a probability that the region of tissue will experience BCR. Combined classification circuit 657 computes the probability based, at least in part, on the combined feature set.

Combined classification circuit 657 is further configured to generate a classification of the region of tissue as likely to experience BCR or unlikely to experience BCR. Combined classification circuit 657 generates the classification based, at least in part, on the probability.

In one embodiment, combined classification circuit 657 is further configured to receive the combined feature set from feature extraction circuit 655 and compute a second probability that the region of tissue will experience metastasis. Combined classification circuit 657 computes the second probability based, at least in part, on the combined feature set. In this embodiment, combined classification circuit 657 is further configured to generate a second classification of the region of tissue as likely to experience metastasis or unlikely to experience metastasis. Combined classification circuit 657 generates the second classification based, at least in part, on the second probability.

In one embodiment, combined classification circuit 657 is a machine learning classifier or includes a machine learning circuit configured to compute the probability or the second probability based, at least in part, on the combined feature set using a random forest machine learning approach. In another embodiment, combined classification circuit 657 is configured as another different type of machine learning classifier, including a support vector machine (SVM), a linear discriminant analysis (LDA) classifier, a quadratic discriminant analysis (QDA) classifier, a convolutional neural network (CNN), or other type of machine learning or deep learning classifier.

Figure 7:
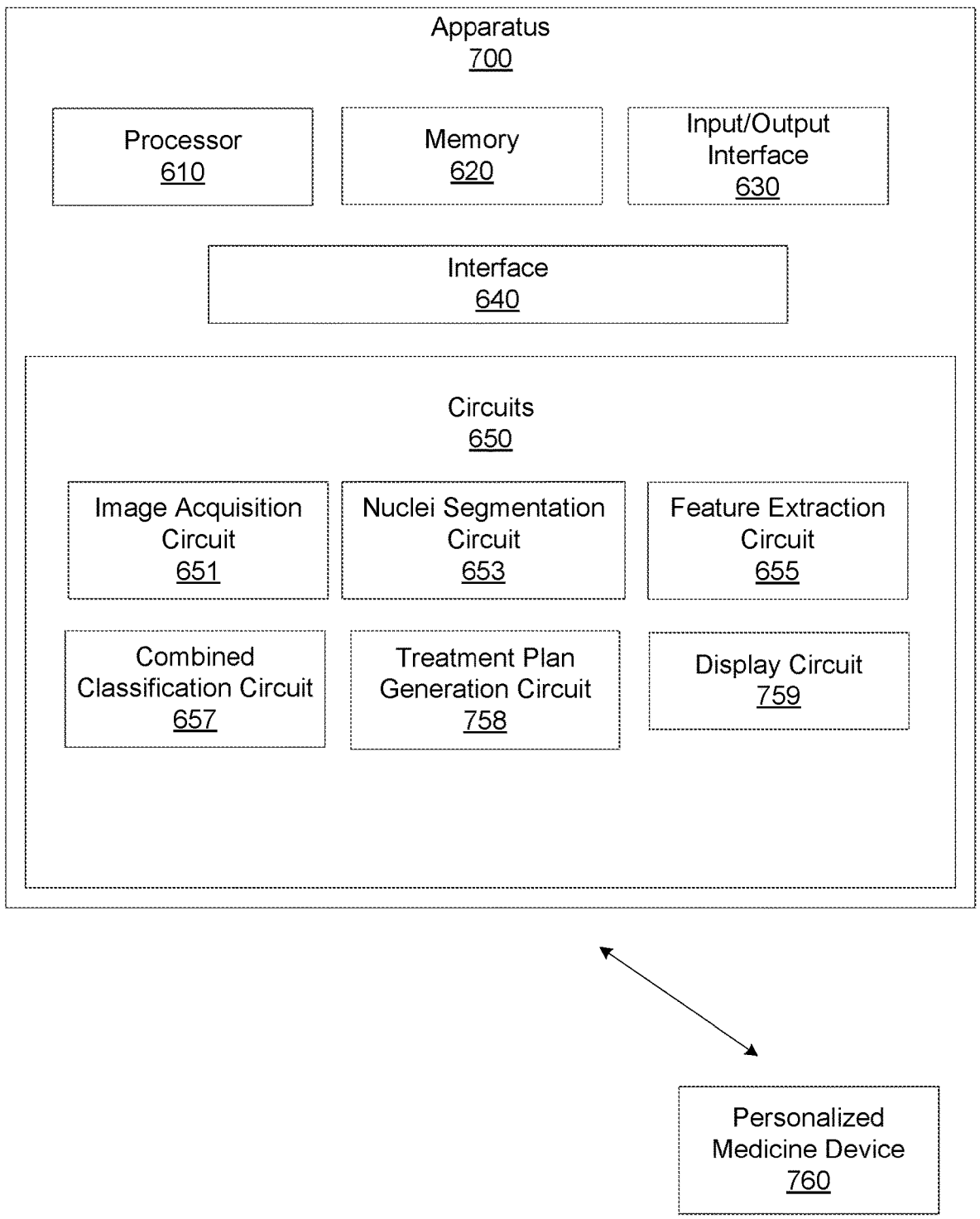
FIG. 7 illustrates an example apparatus for predicting BCR or metastasis.

FIG. 7 illustrates an example apparatus 700 that is similar to apparatus 600 but that includes additional elements and details. In one embodiment, apparatus 700 further includes a treatment plan generation circuit 758 configured to generate a PCa treatment plan based, at least in part, on the classification or the second classification. In one embodiment, apparatus 700 further includes a display circuit 759 configured to display the treatment plan, the probability, the classification, the second probability, the second classification, the H&E stained image, or the Feulgen stained image.

Treatment plan generation circuit 758 is configured to generate a cancer treatment plan for the patient of whom the set of digitized images was acquired based, at least in part, on the classification, the set of digitized images, the combined feature set, the probability, or the second probability. Defining a personalized cancer treatment plan facilitates delivering a particular treatment that will be therapeutically active to the patient, while minimizing negative or adverse effects experienced by the patient. For example, the cancer treatment plan may suggest a surgical treatment, may define an immunotherapy agent dosage or schedule, or a chemotherapy agent dosage or schedule, for a patient identified as likely to experience BCR or metastasis. For a patient classified as unlikely to experience BCR or metastasis, other treatments may be suggested.

In another embodiment, apparatus 600 or apparatus 700 may control a CADx system to classify the region of tissue represented in the H&E stained image or the Feulgen stained image based, at least in part, on the probability or the second probability, or the classification or the second classification. In other embodiments, other types of CADx systems may be controlled, including CADx systems for predicting BCR or metastasis in other tissue presenting other, different pathologies that may be distinguished based on features extracted from both H&E and Feulgen stained images. For example, embodiments described herein may be employed to predict disease progression or metastasis based on probabilities computed from features extracted from both H&E and Feulgen stained images by a machine learning classifier in breast cancer (BCa), kidney disease, lung cancer, or brain pathologies.

Display circuit 759 is configured to display the treatment plan, the probability, the classification, the second probability, the second classification, the H&E stained image, or the Feulgen stained image. In one embodiment, display circuit 759 is configured to display the treatment plan, the probability, the classification, the second probability, the second classification, the H&E stained image, or the Feulgen stained image on a computer monitor, a smartphone display, a tablet display, or other displays. Displaying the treatment plan, the probability, the classification, the second probability, the second classification, the H&E stained image, or the Feulgen stained image may also include printing the treatment plan, the probability, the classification, the second probability, the second classification, the H&E stained image, or the Feulgen stained image. Display circuit 759 may also control a CADx system, a monitor, or other display, to display operating parameters or characteristics of image acquisition circuit 651, nuclei segmentation circuit 653, feature extraction circuit 655, or combined classification circuit 657, including a machine learning classifier, during both training and testing, or during clinical operation of apparatus 600 or apparatus 700.

In another embodiment of apparatus 600 or 700, the set of circuits 650 further includes a training circuit configured to train combined classification circuit 657. Training combined classification circuit 657 may include training a machine learning classifier. In one embodiment, the training circuit is configured to access a dataset of digitized images of a region of tissue demonstrating PCa. In this embodiment, the machine learning classifier is trained and tested using a training set of images and a testing set of images. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed.

FIG. 7 also illustrates a personalized medicine device 760. Personalized medicine device 760 may be, for example, a CADx system, a PCa BCR or metastasis prediction system, or other type of personalized medicine device that may be used to facilitate the prediction of cancer progression or metastasis. In one embodiment, treatment plan generation circuit 758 may control personalized medicine device 760 to display the treatment plan, the probability, the classification, the second probability, the second classification, the H&E stained image, or the Feulgen stained image on a computer monitor, a smartphone display, a tablet display, or other displays.

Embodiments described herein, including at least apparatus 600 and 700, resolve features extracted from the set of digitized images at a higher order or higher level than a human can resolve in the human mind or with pencil and paper. For example, the global cell graph feature, the local cell graph feature, the shape feature, or the cell orientation entropy (COrE) feature are not biological properties of cancerous tissue that a human eye can perceive. A human prostate does not include a COrE feature, a Delaunay triangulation plot, or a minimum spanning tree, and these features cannot be stored in a human mind. The set of radiomic features provided to the machine learning classifier is of a different nature than the tumor or TAB regions represented in the image. The first probability or the second probability computed by combined classification circuit 657 are of a fundamentally different nature than the set of digitized images, or of the tissue from which the images were generated.

Displaying the treatment plan, the probability, the classification, the second probability, the second classification, the H&E stained image, or the Feulgen stained image involves but is not limited to extracting and changing the character of information present in a region of tissue (e.g. biological tissue), to a radiological image (e.g. CT image), to changing the information present in the image to information of a different character in the set of radiomics features, the probability, and the treatment plan. Embodiments described herein further transform the character of information to information suitable for display on, for example, a computer monitor, a smartphone display, a tablet display, or other displays. Thus, embodiments described herein use a combined order of specific rules, elements, or components that render information into a specific format that is then used and applied to create desired results more accurately, more consistently, and with greater reliability than existing approaches.

Figure 9:
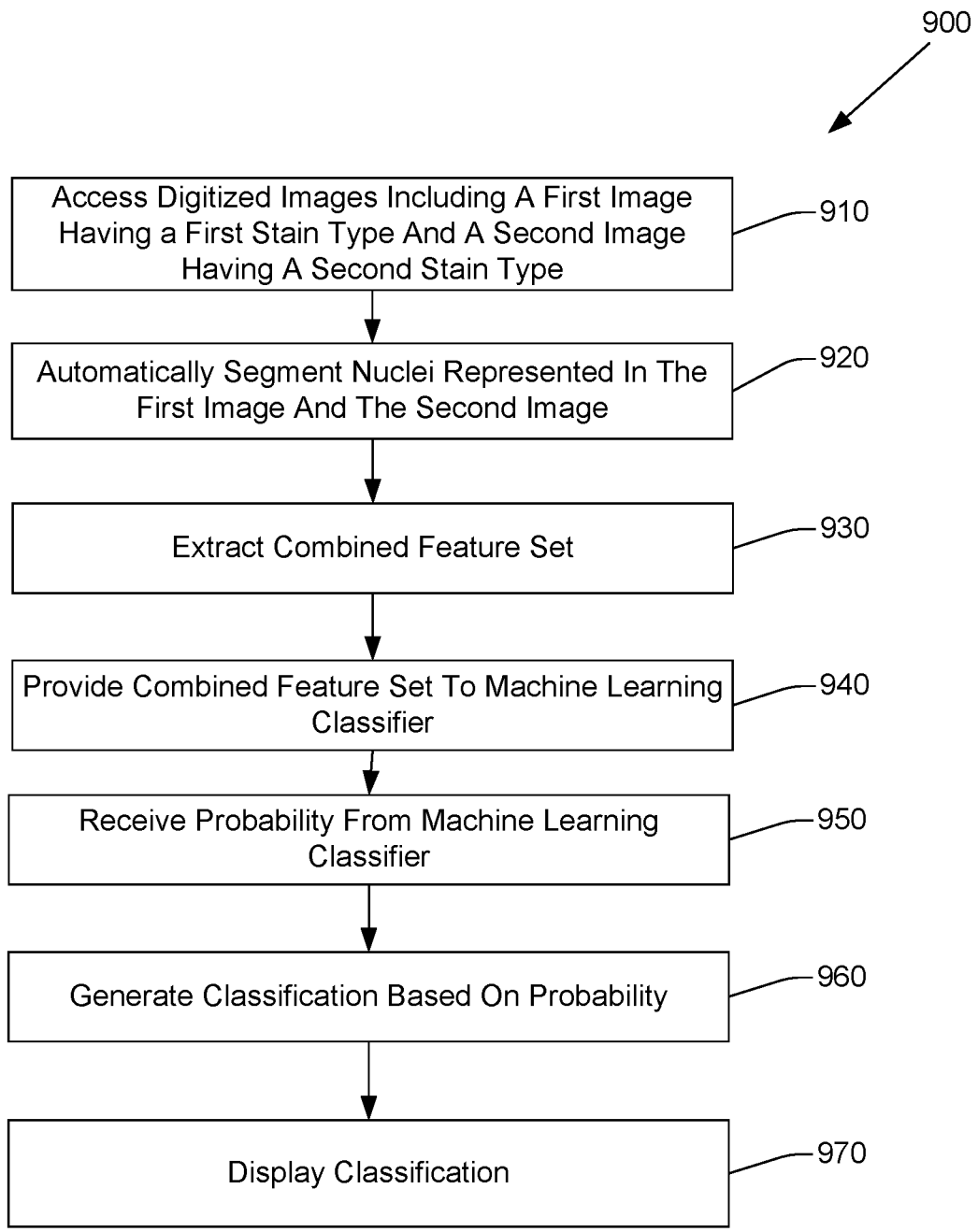
FIG. 9 illustrates an example method for predicting BCR or metastasis.

FIG. 9 illustrates a computerized method 900 for predicting PCa BCR or metastasis. Method 900 may, in one embodiment, be implemented by apparatus 600 or apparatus 700, or computer 800. Method 900 includes, at 910 accessing a set of digitized images of a region of tissue demonstrating cancerous pathology. The region includes a tumor region and tumor adjacent benign (TAB) region. The set of digitized images includes a first image having a first stain type, and a second image having a second, different stain type. Accessing the set of digitized images includes acquiring electronic data, reading from a computer file, receiving a computer file, reading from a computer memory, or other computerized activity.

Method 900 also includes, at 920, automatically segmenting cellular nuclei represented in the first image and the second image. In one embodiment, a watershed approach is used to automatically segment cellular nuclei. In another embodiment, other segmentation techniques may be employed.

Method 900 also includes, at 930, generating a combined feature set by extracting at least one nuclear morphology feature from each of a tumor region represented in the first image, a TAB region represented in the first region, a tumor region represented in the second image, and a TAB region represented in the second image. The at least one nuclear morphology feature is based on the segmented cellular nuclei. In one embodiment, the combined feature set includes a global cell graph feature, a local cell graph feature, a shape feature, a cell orientation entropy (COrE) feature, and a texture feature. In one embodiment, the combined feature set includes at least ten features. In another embodiment, the combined feature set may include other different numbers of features.

Method 900 also includes, at 940, providing the combined feature set to a machine learning classifier. The machine learning classifier, in one embodiment, is a random forest classifier. Providing the combined feature set includes acquiring electronic data, reading from a computer file, receiving a computer file, reading from a computer memory, or other computerized activity.

Method 900 also includes, at 950, receiving, from the machine learning classifier, a probability that the region of tissue will experience BCR, where the machine learning classifier computes the probability based on the combined feature set. Receiving the probability includes acquiring electronic data, reading from a computer file, receiving a computer file, reading from a computer memory, or other computerized activity. The machine learning classifier may be a random forest classifier, or other type of machine learning or deep learning classifier.

Method 900 also includes, at 960, generating a classification of the region of tissue as likely to experience BCR or unlikely to experience BCR. The classification is based, at least in part, on the probability.

Method 900 further includes, at 970, displaying the classification and at least one of the probability, the combined feature set, the first image, or the second image.

In one embodiment, method 900 further includes receiving, from the machine learning classifier, a second probability that the region of tissue will experience metastasis, where the machine learning classifier computes the second probability based on the combined feature set. In this embodiment, method 900 further includes generating a second classification of the region of tissue as likely to experience metastasis or unlikely to experience metastasis based, at least in part, on the second probability. In this embodiment, method 900 additionally includes displaying the second classification and at least one of the second probability, the combined feature set, the first image, or the second image.

Improved identification or classification of patients who will experience BCR or metastasis may produce the technical effect of improving treatment efficacy by increasing the accuracy of and decreasing the time required to treat patients demonstrating BCR or metastasis in PCa or other forms of cancerous pathology. Treatments and resources, including expensive immunotherapy agents or chemotherapy may be more accurately tailored to patients with a likelihood of benefiting from said treatments and resources, including responding immunotherapy or chemotherapy, so that more appropriate treatment protocols may be employed, and expensive resources are not wasted. Controlling a personalized medicine system, a CADx system, or a cancer BCR or metastasis prediction system based on improved, more accurate identification or classification of patients who will experience BCR or metastasis further improves the operation of the system, since unnecessary operations will not be performed.

Using a more appropriately modulated treatment may lead to less aggressive therapeutics being required for a patient or may lead to avoiding or delaying a radical prostatectomy, a biopsy, a resection, or other invasive procedure. When patients experiencing PCa who will more likely experience BCR or metastasis are more quickly and more accurately distinguished from patients who will not, patients most at risk may receive a higher proportion of scarce resources (e.g., therapeutics, physician time and attention, hospital beds) while those less likely to benefit from the treatment may be spared unnecessary treatment, which in turn spares unnecessary expenditures and resource consumption. Example methods, apparatus, and other embodiments may thus have the additional effect of improving patient outcomes compared to existing approaches.

While FIGS. 2-5, and 9 illustrate various actions occurring in serial, it is to be appreciated that various actions illustrated in FIG. 2-5 or 9 could occur substantially in parallel. By way of illustration, a first process could involve segmenting cellular nuclei represented in an H&E stained image, a second process could involve extracting radiomic features, and a third process could involve generating a probability based on the extracted features. While three processes are described, it is to be appreciated that a greater or lesser number of processes could be employed and that lightweight processes, regular processes, threads, and other approaches could be employed.

In one example, a method may be implemented as computer executable instructions. Thus, in one example, a computer-readable storage device may store computer executable instructions that if executed by a machine (e.g., computer, processor) cause the machine to perform methods or operations described or claimed herein including methods or operations 200, 300, 400, 500, or 900. While executable instructions associated with the listed methods are described as being stored on a computer-readable storage device, it is to be appreciated that executable instructions associated with other example methods described or claimed herein may also be stored on a computer-readable storage device. In different embodiments the example methods described herein may be triggered in different ways. In one embodiment, a method may be triggered manually by a user. In another example, a method may be triggered automatically.

Figure 8:
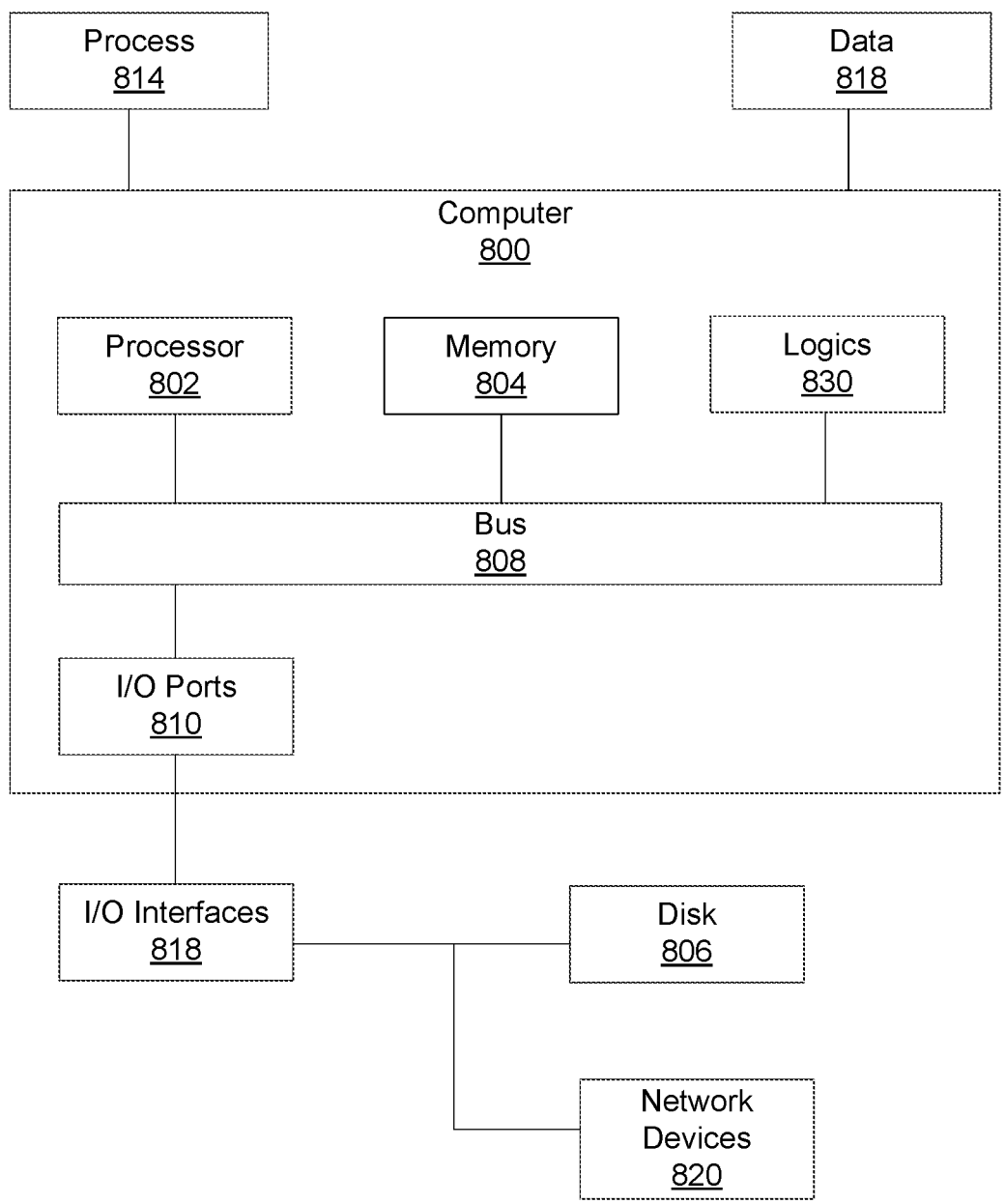
FIG. 8 illustrates an example computer in which example embodiments described herein may operate.

FIG. 8 illustrates an example computer 800 in which example methods or operations illustrated herein can operate and in which example methods, apparatus, circuits, operations, or logics may be implemented. In different examples, computer 800 may be part of a personalized medicine system, a cancer BCR or metastasis prediction system, a digital whole slide scanner, a CT system, may be operably connectable to a CT system, an MRI system, a personalized medicine system, or a digital whole slide scanner, or may be part of a CADx system.

Computer 800 includes a processor 802, a memory 804, and input/output (I/O) ports 810 operably connected by a bus 808. In one example, computer 800 may include a set of logics or circuits 830 that perform a method of predicting cancer BCR or metastasis using a machine learning classifier. Thus, the set of circuits 830, whether implemented in computer 800 as hardware, firmware, software, and/or a combination thereof may provide means (e.g., hardware, firmware, circuits) for predicting cancer BCR or metastasis based on features extracted from both Feulgen stained images of a region of tissue and H&E stained images of the region of tissue. In different examples, the set of circuits 830 may be permanently and/or removably attached to computer 800.

Processor 802 can be a variety of various processors including dual microprocessor and other multi-processor architectures. Processor 802 may be configured to perform steps of methods claimed and described herein. Memory 804 can include volatile memory and/or non-volatile memory. A disk 806 may be operably connected to computer 800 via, for example, an input/output interface (e.g., card, device) 818 and an input/output port 810. Disk 806 may include, but is not limited to, devices like a magnetic disk drive, a tape drive, a Zip drive, a flash memory card, or a memory stick. Furthermore, disk 806 may include optical drives like a CD-ROM or a digital video ROM drive (DVD ROM). Memory 804 can store processes 814 or data 817, for example. Data 817 may, in one embodiment, include digitized images of stained slides of a region of tissue demonstrating PCa, CT images of a region of tissue demonstrating PCa, or other radiological imagery. Disk 806 or memory 804 can store an operating system that controls and allocates resources of computer 800.

Bus 808 can be a single internal bus interconnect architecture or other bus or mesh architectures. While a single bus is illustrated, it is to be appreciated that computer 800 may communicate with various devices, circuits, logics, and peripherals using other buses that are not illustrated (e.g., PCIE, SATA, Infiniband, 1394, USB, Ethernet).

Computer 800 may interact with input/output devices via I/O interfaces 818 and input/output ports 810. Input/output devices can include, but are not limited to, CT systems, MRI systems, digital whole slide scanners, an optical microscope, a keyboard, a microphone, a pointing and selection device, cameras, video cards, displays, disk 806, network devices 820, or other devices. Input/output ports 810 can include but are not limited to, serial ports, parallel ports, or USB ports.

Computer 800 may operate in a network environment and thus may be connected to network devices 820 via I/O interfaces 818 or I/O ports 810. Through the network devices 820, computer 800 may interact with a network. Through the network, computer 800 may be logically connected to remote computers. The networks with which computer 800 may interact include, but are not limited to, a local area network (LAN), a wide area network (WAN), or other networks, including the cloud.

Examples herein can include subject matter such as an apparatus, a personalized medicine system, a CADx system, a processor, a system, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting cancer recurrence, or cancer metastasis, according to embodiments and examples described.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer executable instructions that when executed control a processor to perform operations, the operations including:
    accessing a set of images of a region of tissue demonstrating prostate cancer (PCa), where an image has a plurality of pixels, a pixel having an intensity, where the region of tissue includes a tumor region and a tumor adjacent benign (TAB) region, and where the set of images includes a digitized hematoxylin and eosin (H&E) stained image of the region of tissue, and a Feulgen stained image of the region of tissue;
    segmenting cellular nuclei represented in the H&E stained image and the Feulgen stained image using a watershed approach;
    extracting a first set of radiomic features from the H&E stained image based, at least in part, on the segmented nuclei;
    extracting a second set of radiomic features from the Feulgen stained image based, at least in part, on the segmented nuclei;
    generating a combined feature set from the first set of radiomic features and the second set of radiomic features, where the combined feature set includes at least one feature extracted from the tumor region represented in the H&E stained image and at least one feature extracted from the TAB region represented in the H&E stained image, and at least one feature extracted from the tumor region represented in the Feulgen stained image and at least one feature extracted from the TAB region represented in the Feulgen stained image, wherein the combined feature set includes ten features;

providing the combined feature set to a machine learning classifier;

receiving, from the machine learning classifier, a probability that the region of tissue will experience biochemical recurrence (BCR), where the probability is based, at least in part, on the combined feature set; and generating a classification of the region of tissue as likely to experience BCR or unlikely to experience BCR based, at least in part, on the probability.

2. The non-transitory computer-readable storage device of claim 1, the operations further including:

receiving, from the machine learning classifier, a second probability that the region of tissue will experience metastasis, where the second probability is based, at least in part, on the combined feature set; and generating a classification of the region of tissue as likely to experience metastasis or unlikely to experience metastasis based, at least in part, on the second probability.

3. The non-transitory computer-readable storage device of claim 1, the operations further including:

generating a PCa treatment plan based, at least in part, on the classification.

4. The non-transitory computer-readable storage device of claim 1, where the H&E stained image is a digitized image of an H&E slide of the region of tissue scanned at a resolution of 0.5 microns per pixel.

5. The non-transitory computer-readable storage device of claim 1, where the Feulgen stained image is a digitized image of a Feulgen stained slide of the region of tissue scanned at a resolution of 0.5 microns per pixel.

6. The non-transitory computer-readable storage device of claim 1, where the first set of radiomic features includes a global cell graph feature, a local cell graph feature, a shape feature, a cell orientation entropy (COrE) feature, and a texture feature, and where the second set of radiomic features includes a global cell graph feature, a local cell graph feature, a shape feature, a cell orientation entropy (COrE) feature, and a texture feature.

7. The non-transitory computer-readable storage device of claim 6, where a global cell graph feature or a local cell graph feature is a Voronoi diagram, a Delaunay triangulation plot, or a minimum spanning tree.

8. The non-transitory computer-readable storage device of claim 1, where the machine learning classifier is a Random Forest classifier.

9. The non-transitory computer-readable storage device of claim 1, the operations further including training the machine learning classifier.

10. An apparatus for predicting prostate cancer (PCa) biochemical recurrence (BCR), the apparatus comprising:

a processor;

a memory configured to store a set of digitized images of a region of tissue demonstrating PCa, where a member of set of digitized images has a plurality of pixels, a pixel having an intensity, where the region of tissue includes a tumor region and a tumor adjacent benign (TAB) region;

an input/output (I/O) interface;

a set of circuits comprising an image acquisition circuit, a nuclei segmentation circuit, a feature extraction circuit, and a combined classification circuit; and an interface that connects the processor, the memory, the I/O interface, and the set of circuits;

the image acquisition circuit configured to access the set of digitized images, where the set of digitized images includes a hematoxylin and eosin (H&E) stained image of the region of tissue, and a Feulgen stained image of the region of tissue;

the nuclei segmentation circuit configured to segment cellular nuclei represented in the H&E stained image and the Feulgen stained image using a watershed approach;

the feature extraction circuit configured to:

extract an H&E set of radiomic features from the tumor region and the TAB region of the H&E stained image based, at least in part, on the segmented nuclei;

extract a Feulgen set of radiomic features from the tumor region and the TAB region of the Feulgen stained image based, at least in part, on the segmented nuclei;

generate a combined feature set from the H&E set and the Feulgen set, where the combined feature set includes at least one feature extracted from each of the tumor region and the TAB region of the H&E stained image, and at least one feature extracted from each of the tumor region and the TAB region of the Feulgen stained image, wherein the combined feature set includes ten features; and provide the combined feature set to the combined classification circuit;

the combined classification circuit configured to:

receive the combined feature set from the feature extraction circuit;

compute a probability that the region of tissue will experience BCR based, at least in part, on the combined feature set; and generate a classification of the region of tissue as likely to experience BCR or unlikely to experience BCR based, at least in part, on the probability.

11. The apparatus of claim 10, where the combined feature set includes a global cell graph feature, a local cell graph feature, a shape feature, a cell orientation entropy (COrE) feature, and a texture feature.

12. The apparatus of claim 10, where the combined classification circuit is further configured to:

receive the combined feature set from the feature extraction circuit;

compute a second probability that the region of tissue will experience metastasis based, at least in part, on the combined feature set; and generate a second classification of the region of tissue as likely to experience metastasis or unlikely to experience metastasis based, at least in part, on the second probability.

13. The apparatus of claim 12, where the combined classification circuit is a machine learning classifier configured to compute the probability or the second probability based, at least in part, on the combined feature set using a random forest machine learning approach.

14. The apparatus of claim 12, the set of circuits further comprising:

a treatment plan generation circuit configured to generate a PCa treatment plan based, at least in part, on the classification or the second classification; and a display circuit configured to display the treatment plan, the probability, the classification, the second probability, the second classification, the H&E stained image, or the Feulgen stained image.

15. A non-transitory computer-readable storage device storing computer-executable instructions that when executed by a computer control the computer to perform a method for predicting biochemical recurrence (BCR), the method comprising:

accessing a set of digitized images of a region of tissue demonstrating cancerous pathology, the region having a tumor region and tumor adjacent benign (TAB) region, the set of digitized images including a first image having a first stain type, and a second image having a second, different stain type;

automatically segmenting cellular nuclei represented in the first image and the second image using a watershed approach;

generating a combined feature set by extracting at least one nuclear morphology feature from each of a tumor region represented in the first image, a TAB region represented in the first region image, a tumor region represented in the second image, and a TAB region represented in the second image, where the at least one nuclear morphology feature is based on the segmented cellular nuclei, wherein the combined feature set includes ten features;

providing the combined feature set to a machine learning classifier;

receiving, from the machine learning classifier, a probability that the region of tissue will experience BCR, where the machine learning classifier computes the probability based on the combined feature set;

generating a classification of the region of tissue as likely to experience BCR or unlikely to experience BCR based, at least in part, on the probability; and displaying the classification and at least one of the probability, the combined feature set, the first image, or the second image.

16. The non-transitory computer-readable storage device of claim 15, the method further comprising:

receiving, from the machine learning classifier, a second probability that the region of tissue will experience metastasis, where the machine learning classifier computes the second probability based on the combined feature set;

generating a second classification of the region of tissue as likely to experience metastasis or unlikely to experience metastasis based, at least in part, on the second probability; and displaying the second classification and at least one of the second probability, the combined feature set, the first image, or the second image.

* * * * *

UNITED STATES PATENT AND TRADEMARK OFFICE
CERTIFICATE OF CORRECTION

PATENT NO. : 10,776,607 B2
APPLICATION NO. : 15/983397
DATED : September 15, 2020
INVENTOR(S) : Anant Madabhushi et al.

It is certified that error appears in the above-identified patent and that said Letters Patent is hereby corrected as shown below:

In the Specification

Column 1, Lines 15 through 21; please replace "This invention was made with government support under grants DK098503, CA179327, CA195152, CA199374, CA202752, RR012463 and CA208236 awarded by the National Institutes of Health. Also, grants W81XWH-13-1-0418, W81XWH-14-1-0323, and W81XWH-16-1-0329 awarded by the Department of Defense. The government has certain rights in the invention." with --This invention was made with government support under grants DK098503, CA179327, CA195152, CA199374, CA202752, RR012463 and CA208236 awarded by the National Institutes of Health. Also, grants W81XWH-13-1-0418, W81XWH-14-1-0323, W81XWH-15-1-0558, and W81XWH-16-1-0329 awarded by the Department of Defense. The government has certain rights in the invention.--

Signed and Sealed this
Twenty-first Day of September, 2021

Drew Hirshfeld
*Performing the Functions and Duties of the
Under Secretary of Commerce for Intellectual Property and
Director of the United States Patent and Trademark Office*